United States Patent [19]

Pellacini et al.

[11] Patent Number: 5,157,143

[45] Date of Patent: Oct. 20, 1992

[54] DIASTEREOSELECTIVE PROCESS FOR THE PREPARATION OF INTERMEDIATES USEFUL FOR THE SYNTHESIS OF PEPTIDE DERIVATIVES

[75] Inventors: Franco Pellacini, Sesto S. Giovanni; Dario Chiarino, Monza; Angelo Carenzi, Busto Arsizio, all of Italy

[73] Assignee: Zambon Group S.p.A., Vicenza, Italy

[21] Appl. No.: 350,462

[22] Filed: May 11, 1989

[30] Foreign Application Priority Data

May 11, 1988 [IT] Italy ................... 20542 A/88

[51] Int. Cl.⁵ .......................................... C07C 331/00
[52] U.S. Cl. ........................................ 560/12; 560/9; 560/22; 560/24; 560/27; 560/29; 560/30; 560/31; 560/32; 560/33
[58] Field of Search ............... 560/9, 12, 22, 27, 29; 562/444, 24, 30, 31, 32, 33

[56] References Cited

U.S. PATENT DOCUMENTS 4,281,180  7/1981  Umezawa ........................... 562/444
4,352,752  10/1982  Ojima ................................. 562/444

*Primary Examiner*—Michael L. Shippen
*Attorney, Agent, or Firm*—Stevens, Davis, Miller & Mosher

[57] ABSTRACT

A diastereoselective process for the preparation of compounds of formula $$R-CH_2-\underset{*}{CH}(NHR_1)-\underset{*}{CH}(OH)-COOH \quad (I)$$

(wherein R and $R_1$ have the meanings reported in the specification and the asterisks show the asymmetric carbon atoms) starting from the corresponding N-protected 2-amino-3-aryl-propan-1-ol is described.

The compounds of formula I are intermediates useful for the synthesis of pharmacologically active peptides.

6 Claims, No Drawings

DIASTEREOSELECTIVE PROCESS FOR THE PREPARATION OF INTERMEDIATES USEFUL FOR THE SYNTHESIS OF PEPTIDE DERIVATIVES

The present invention relates to a diastereoselective process for the preparation of intermediates useful for the synthesis of peptide derivatives and, more particularly, it relates to a diastereoselective process for the preparation of N-protected derivatives of 3-amino-4-aryl-2-hydroxy-butanoic acid of formula $$R-CH_2-\overset{*}{\underset{NHR_1}{CH}}-\overset{*}{\underset{OH}{CH}}-COOH \quad (I)$$

wherein
R represents a phenyl optionally substituted by from 1 to 3 substituents selected among hydroxy, halogen, $C_1-C_6$ alkoxy, $C_1-C_6$ alkyl, phenyl, amino, mono or dialkylamino groups having from 1 to 6 carbon atoms in the alkyl moiety, nitro, mercapto, alkylthio, alkylsulfinyl or alkylsulfonyl groups having from 1 to 6 carbon atoms in the alkyl moiety;
$R_1$ represents a protecting group and the asterisks show the asymmetric carbon atoms;
starting from the corresponding N-protected 2-amino-3-aryl-propan-1-ol.

Most of the compounds of formula I are known and they are described, for example, in J. Med. Chem. 20(4), 1977, 510–15 and in the Japanese patent applications no. 54/9237 and no. 56/90050 (Microbiochemical Research Foundation).

The compounds of formula I wherein R represents a phenyl substituted by an alkylthio, alkylsulfinyl or alkylsulfonyl group are described in the Italian Patent application no. 19791 A/88 in the name of Zambon Group S.p.A. filed on Mar. 16, 1988 now Italian Patent No. 1,216,104, corresponding to European Patent application No. 333,000. The compounds of formula I are useful as intermediates for the synthesis of pharmacologically active peptides of formula $$R-CH_2-\underset{NHR_2}{CH}-\underset{OH}{CH}-CONHR_3 \quad (II)$$

wherein R has the meanings reported in formula I; $R_2$ represents a hydrogen atom or an acyl group and $R_3$ represents a residue of an aminoacid, of a di or tripeptide.

Examples of such compounds are Bestatin [Drugs of the Future, vol. VI, no. 10 (1981), page 604], the compounds showing an inhibitory activity on aminopeptidase B described in British Patent no. 1 510 477 and in U.S. Pat. No. 4,185,156 (Microbiochemical Research Foundation) and in the Italian patent application no. 19791 A/88 (Zambon Group S.p.A.), the anti-hypertensive compounds described in U.S. Pat. No. 4,293,481 (Squibb E. R. and Sons, Inc.) or the analgesic compounds described in the Japanese patent application no. 60/248659 (Microbiochemical Research Foundation). Several syntheses of the intermediates of formula I, and particularly of the intermediate (I, R=unsubstituted phenyl) useful for the preparation of Bestatin have been already described in literature.

However, as far as we know, none of these syntheses is a diastereoselective process.

Each of them, in fact, comprises the optical resolution of a racemic mixture, which is carried out on the compound of formula II or on an intermediate of the synthesis, such as for example a compound of formula I, in order to separate the diastereoisomer with the desired configuration.

Among the different separation methods used in the processes described in literature, there is the optical resolution of diastereoisomeric salts obtained using optically active bases such as brucine (British Patent no. 1 510 477), alpha-phenylethylamine (Japanese patent application no. 58/41848—Nippon Kayaku Co. Ltd.) and S(-)-alpha-methylbenzylamine [J. Antib., 36(6), 1983, 695].

Alternatively, the separation is carried out also by chromatographic methods [J. Antib., 29(5), 1976, 600].

It is clear that the necessity to carry out an optical separation involves an increase of synthetic process costs, particularly in the industrial application.

Such an increase is due to several reasons among which the use of expensive resolving agents or of long and burdensome techniques in the resolution.

Anyhow, the most important reason is the fact that the yield with respect to the isomer with desired configuration cannot exceed, in any case, 50% in a reaction of resolution of a racemic mixture, and, as far as we know, industrial methods to racemize the undesired isomer do not exist.

We have now surprisingly found a diastereoselective process for the preparation of the compounds of formula I which, in addition to the advantage of requesting no optical separation, has further advantages particularly for its better industrial applicability. The diastereoselective process object of the present invention is reported in the following scheme.

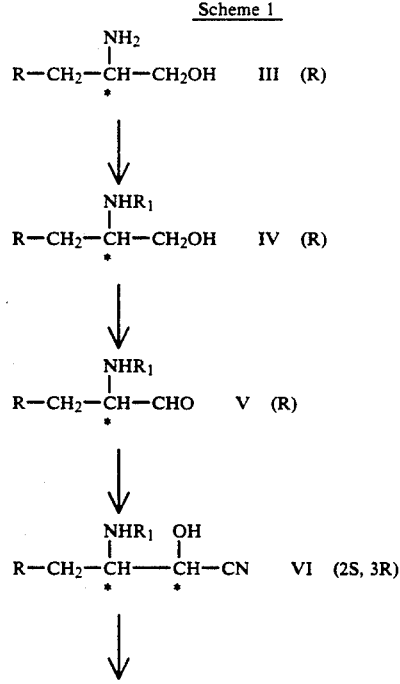

Scheme 1

-continued
Scheme 1

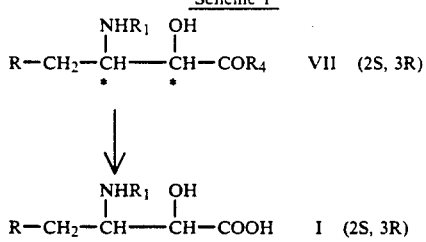

wherein R and $R_1$ have the above reported meanings and $R_4$ represents a $NH_2$ or $C_1-C_3$ alkoxy group.

Starting from an aminoalcohol of formula III with a predetermined configuration and protecting the amino function, the aldehyde of formula V is obtained by subsequent oxidation.

From compound V the cyanohydrin VI is obtained diastereoselectively with (2S,3R) configuration, which gives by hydrolysis, first, the amide or the ester of formula VII and, then, the desired acid I.

The compounds of formula III are known (European patent application no. 167 459 in the name of Albert Rolland S.A.) or they are easily prepared by known methods.

The protection of the amino function in order to obtain the compounds of formula IV is carried out according to usual techniqiues in organic chemistry, especially in peptide chemistry, by reaction of a compound of formula III with a compound of formula $R_1X$ wherein $R_1$ is a protecting group and X represents a halogen atom.

Preferably the halides of carbonic acid esters are used as protecting agents of formula $R_1X$.

Suitable protecting groups ($R_1$) are adamantyloxycarbonyl, t.amyloxycarbonyl, benzhydryloxycarbonyl, benzyloxycarbonyl, p.bromobenzyloxycarbonyl, t.butoxycarbonyl, cyclohexyloxycarbonyl, cyclopentyloxycarbonyl, p.methoxybenzyloxycarbonyl, p.nitrobenzyloxycarbonyl, p.phenylazobenzyloxycarbonyl, 2,2,2-trichloroethoxycarbonyl.

Preferred protecting groups are benzyloxycarbonyl and t.butoxycarbonyl.

The protected aminoalcohol of formula IV is then oxidized in order to obtain the corresponding aldehyde of formula V.

Different oxidation methods, known in organic chemistry, of primary alcohols to prepare aliphatic aldehydes may be used to obtain the compounds V.

Among these, for example, the methods using as oxidizing systems dimethylsulfoxide or piridinium dicromate or potassium bicromate and tetrabutylammonium bromide in phase transfer conditions may be cited.

The preferred oxidizing agent for its better availability and cost is dimethylsulfoxide which is used optionally in the presence of other reagents such as $SO_3$-pyridine-triethylamine complex, tosyl chloride, acetic anhydride or, preferably, oxalyl chloride and triethylamine, in an inert organic solvent.

It is worth noting that the oxidation is selective and it does not affect optional further oxidable groups which are present in the compound of formula IV.

The step of transformation of the aldehyde V in the cyanohydrin VI, which by itself is a further object of the present invention, is carried out by reaction with a suitable silylcyanide in an aprotic solvent at a temperature between −80° C. and room temperature.

The reaction may be optionally carried out in the presence of suitable catalysts such as Lewis acids, for example zinc iodide, zinc chloride, titanium tetrachloride and stannic chloride or such as alkaline cyanides, for example potassium cyanide or its compounds with crown ethers, and sodium cyanide.

Examples of suitable silylcyanides, which may be optionally prepared in situ from the corresponding silylchlorides with potassium cyanide, are trimethylsilylcyanide, triphenylsilylcyanide, phenyldimethylsilylcyanide, ethyldimethylsilylcyanide, t.butyldimethylsilylcyanide, tripropylsilylcyanide.

Among the suitable aprotic solvents there are aromatic hydrocarbons such as benzene and toluene, halogenated hydrocarbons such as chloroform, methylene chloride and dichloroethane, ethers such as ethyl ether, tetrahydrofuran, dioxane, isopropyl ether and t.butylmethylether.

Preferably the reaction is carried out with trimethylsilylcyanide at a temperature between −80° C. and −20° C. The reaction of formation of the cyanohydrin starting from the aldehyde V is diastereoselective.

As far as the two asymmetric centers of the cyanohydrin VI, marked by an asterisk, are concerned, that bearing the amino group has predetermined configuration (R) because it maintains the configuration of the starting aminoalcohol III.

The second asymmetric center is introduced by the reaction of formation of the cyanohydrin.

Surprisingly this reaction of the process object of the present invention acts diastereoselectively giving prevailingly the cyanohydrin VI wherein the carbon atom bearing the hydroxy group has S configuration.

In other words, from the reaction, with very good yield, a mixture of the two diastereoisomeric cyanohydrins (2S,3R) and (2R,3R) is obtained in which the cyanohydrin VI with the configuration (2S,3R) highly prevails.

That allows to use this mixture directly in the following steps of the process without carrying out any resolution.

If desired, the diastereoisomerically pure cyanohydrin VI may be obtained by simple crystallization or suspension in a suitable solvent of the mixture of the two diastereoisomers obtained by the process object of the present invention.

The subsequent step of the process reported in Scheme 1 is the hydrolysis of the cyanohydrin VI.

The hydrolysis is carried out in an acid environment with concentrated inorganic acids, preferably hydrochloric acid, mixed with an organic solvent and at a temperature between 0° C. and room temperature.

The intermediate of formula VII is obtained as an amide ($R_4=NH_2$) when the hydrolysis is carried out with an aqueous acid or, alternatively, as an ester ($R_4=C_1-C_3$ alkoxy) when the hydrolysis is carried out using an alcoholic solution of the inorganic acid.

The intermediate VII is, then, further hydrolized to give the diastereoisomerically pure acid I using a diluted inorganic acid or base, at a temperature between 60° C. and the reflux temperature of the reaction mixture.

Preferably hydrochloric acid or sodium hydroxide at 1N concentration are used.

It is clear that by the process object of the present invention the compounds of formula I in (2R,3S) configuration may be obtained analogously.

In fact, starting from an aminoalcohol of formula III in S configuration, the corresponding aldehyde V with S configuration is obtained by oxidation.

The aldehyde V in S configuration is, then, diastereoselectively transformed in a mixture of the two diastereoisomeric cyanohydrins (2R,3S) and (2S,3S) in which the (2R,3S) cyanohydrin VI highly prevails.

Such a mixture may be directly used in the subsequent steps of hydrolysis to give the compounds of formula I with (2R,3S) configuration.

From a practical point of view it is clear to the man skilled in the art that the process object of the present invention is characterized by a very good industrial applicability and it may be also carried out with a real number of industrial steps lower than those reported in scheme 1.

The aldehyde V, for example, may be prepared in situ from the aminoalcohol IV and directly reacted in the same reaction environment with a suitable silylcyanide to obtain the cyanohydrin VI. From cyanohydrin VI the acid I may be, then, directly obtained by carrying out, for example, the acid hydrolysis first with a concentrated aqueous inorganic acid at room temperature for some hours and then, by diluting with water the reaction mixture, at the reflux temperature.

A preferred embodiment of the process object of the present invention is the preparation of the intermediate of formula I wherein R represents an unsubstituted phenyl, useful for the synthesis of Bestatin.

The acid of formula I (R=phenyl), obtainable according to the process of the invention starting, for example, from the corresponding aminoalcohol of formula III wherein R represents a phenyl, is condensed with a derivative of L-leucine with the carboxy group protected as, for example, benzyl ester, in the presence of condensing agents such as dicyclohexylcarbodiimide and of dihydroxybenzotriazole.

The removal by catalytic hydrogenation of the protecting groups on the amino function and on the carboxy function gives Bestatin (II:R=phenyl, $R_2H$, $R_3$=L-leucine residue).

It is clear that the preparation of Bestatin may be carried out also starting from different aminoalcohols of formula III that is from aminoalcohols with substituents on the aromatic ring which are easily removable or which are easily transformable into removable groups.

The man skilled in the art will select the most suitable step of the process for carrying out the transformation or the removal on the basis of the compatibility of the selected methods with the other functional groups of the molecule.

For example, starting from a compound of formula III wherein R is a nitrophenyl group, the corresponding compound III wherein R is an aminophenyl group may be prepared by reduction.

From this one, by diazotization and reaction with hypophosphite, the aminoalcohol III wherein R is a phenyl group is obtained.

Alternatively, starting from the compounds in which the phenyl is substituted by halogen atoms or by alkyl-thio, alkylsulfinyl or alkylsulfonyl groups, the corresponding unsubstituted derivatives may be obtained by reduction.

The process object of the present invention has several advantages with respect to the known processes for the preparation of the acids of formula I.

The diastereoselectivity of the reaction of the preparation of the cyanohydrin VI allows to obtained the final product I in the desired configuration with very good yields without carrying out any optical resolution.

In addition to the diastereoselectivity, it is clear to the man skilled in the art that a further advantage of the process of the invention is represented by the fact that the protective group $R_1$, introduced at the beginning of the process on the aminoalcohol III, is present also on the final compound of formula I, that is also after the hydrolysis reaction.

The preservation of the protecting group, which is necessary in the subsequent condensation reaction to give the compounds of formula II, is very important from a practical point of view because it eliminates the need to carry out a further protecting reaction on the intermediate I contrary to what described for the known processes in literature.

It is important also to underline that the synthesis of the compounds of formula II according to the process object of the present invention has overall yields better than that of known processes.

In order to better illustrate the present invention without limiting it, the following examples are now given.

EXAMPLE 1

(2S,3R)-3-benzyloxycarbonylamino-4-phenyl-2-hydroxy-butanonitrile

Dimethylsulfoxide (22.7 ml; 0.320 moles) dissolved in methylene chloride (50 ml) under stirring at −70° C., and, in succession under the same conditions, a solution of (R)-2-benzyloxycarbonylamino-3-phenyl-propan-1-ol (40 g; 0.140 moles) in a mixture of methylene chloride (200 ml) and dimethylsulfoxide (4 ml) were added dropwise to a solution of oxalyl chloride (13.2 ml; 0.155 moles), freshly distilled, in methylene chloride (160 ml).

After 15 minutes, always at −70° C., triethylamine (43.2 ml; 0.310 moles) was added dropwise.

The reaction mixture was kept under stirring for an hour at −70° C. and then, under the same conditions, a solution of trimethylsilylcyanide (20 ml; 0.154 moles) in methylene chloride (40 ml) was added dropwise.

The reaction mixture was kept at −70° C. for 4 hours and then the temperature was allowed to arise very slowly (10-12 hours) up to the room value.

Water (400 ml) was added, the organic phase was separated and washed twice with water (400 ml), separated again and dried on sodium sulphate.

After evaporation under reduced pressure, the residue was dissolved in tetrahydrofuran (400 ml) and to this solution, cooled at +10° C., hydrochloric acid 1N (56 ml) was added dropwise. The solution was kept under stirring for 30 minutes at room temperature and, then, an aqueous saturated sodium chloride solution (500 ml) and ethyl ether (500 ml) were added.

The mixture was stirred, the organic phase was separated, dried on sodium sulphate and, after evaporation of the solvent, a crude (49 g) was obtained, treated with isopropyl ether (200 ml) for two hours under stirring at room temperature, filtered and dried under vacuum at 50° C.

A solid was obtained (32 g) which resulted to be a mixture of (2S,3R) and (2R,3R)-3-benzyloxycarbonylamino-4-phenyl-2-hydroxybutanonitrile in ratio 97:3 from HPLC analysis (Brownlee Silica column 4.6×220 mm, 5 μm—eluent hexane: ethanol=97.7:2.3, flow 1 ml/min, UV 220 nm). The pure diastereoisomer (2S,3R) was obtained by cristallization from t.butylmethylether.

m.p. 112°–114° C.

$[\alpha]_D^{20} = +88.5°$ (c=1%, DMF)

$^1$H-NMR (200 MHz, CDCl$_3$—TMS): delta (ppm): $\nu_A = 3.12 - \nu_B = 2.89$ (AB portion of an ABX system, $J_{AB} = 14.0$ Hz, $J_{AX} = 6.3$ Hz, $J_{BX} = 8.9$ Hz, 2H); 4.06 (m, 1H); 4.51–4.61 (m, 2H); 5.07 (s, 2H); 5.38 (d, 1H, J=8.2 Hz); 7.16–7.41 (m, 10H).

EXAMPLE 2

(2S,3R)-3-benzyloxycarbonylamino-4-phenyl-2-hydroxy-butanonitrile

Trimethylsilylcyanide (2.6 ml; 0.019 moles) was added dropwise, under stirring and at room temperature to a solution of (R)-2-benzyloxycarbonylamino-3-phenyl-propanal (4.6 g; 0.016 moles) in tetrahydrofuran (45 ml).

After 24 hours at room temperature, hydrochloric acid 1N (6.2 ml) was added, always at this temperature.

The reaction mixture was kept under stirring at room temperature for 30 minutes, then ethyl ether (50 ml) was added and the aqueous phase was saturated with sodium chloride.

The phases were separated and the aqueous phase was treated again with ethyl ether (50 ml). The organic phases were collected, dried on sodium sulphate and evaporated to dryness, giving a crude (5 g).

A portion of this crude (4.38 g) was crystallized from a mixture of petroleum ether (36 ml) and ethyl acetate (6 ml).

(2S,3R)-3-benzyloxycarbonylamino-4-phenyl-2-hydroxy-butanonitrile (2.37 g), containing a little percentage (4%) of (2R,3R) isomer, was obtained.

Overall yield 54.5%—m.p. 112°–114° C.

EXAMPLE 3

(2S,3R)-3-benzyloxycarbonylamino-4-phenyl-2-hydroxy-butanamide

Concentrated hydrochloric acid (500 ml) was added at +10° C. to a solution of (2S,3R)-3-benzyloxycarbonylamino-4-phenyl-2-hydroxybutanonitrile (30 g; 0.096 moles), prepared as described in example 1 or 2, in dioxane (500 ml).

The reaction mixture was kept under stirring at room temperature for 6 hours and, then, poured into water (5 l).

After extraction with ethyl acetate (3×2 l), the organic phase was dried on sodium sulphate and evaporated to dryness.

A solid, which was suspended in isopropyl ether and filtered, was obtained.

After drying under vacuum at 60° C., a product (25.5 g; 80% yield), resulting to be a mixture of (2S,3R) and (2R,3R)-3-benzyloxycarbonylamino-4-phenyl-2-hydroxy-butanamide in ratio 98:2 from HPLC analysis (Browler RP 18 column 22 cm×4.6 mm 5 μm—eluent water:methanol=44:56, flow 1 ml/min, UV 220 nm), was obtained. A small amount of this product (1 g) was crystallized from isopropyl acetate (12 ml) giving the pure (2S,3R) diastereoisomer (0.8 g) with m.p. 145°–147° C.

$[\alpha]_D^{20} = +39.4°$ (c=1%, DMF)

$^1$H-NMR (200 MHz, CD$_3$OD—TMS): delta (ppm): 7.37–7.13 (m, 10H); $\nu_A = 5.01 - \nu_B = 4.95$ (ABq, $J_{AB} = 12.6$ Hz, 2H); 4.25 (m, 1H); 3.98 (d, 1H, J=2.3 Hz); $\nu_A = 2.92 - \nu_B = 2.86$ (AB portion of an ABX system, $J_{AB} = 13.5$ Hz, $J_{AX} = 7.7$ Hz, $J_{BX} = 7.9$ Hz, 2H).

EXAMPLE 4

(2S,3R)-3-benzyloxycarbonylamino-4-phenyl-2-hydroxy-butanamide

Concentrated hydrochloric acid (8.5 ml) was added dropwise, under stirring at +10° C. to a solution of (2S,3R)-3-benzyloxycarbonylamino-4-phenyl-2-hydroxy-butanonitrile (0.5 g; 0.0016 moles), prepared as described in example 1 or 2, in dioxane (8.5 ml).

The temperature was left arising up to the room value and the reaction mixture was kept under stirring at this temperature for 6 hours.

Then, the mixture was poured into water (50 ml) and extracted with ethyl ether (50 ml).

After drying on sodium sulphate and evaporation of the solvent under reduced pressure, (2S,3R)-3-benzyloxycarbonylamino-4-phenyl-2-hydroxy-butanamide (0.47 g; 89.4% yield), with the same spectroscopic and analytical characteristics of the compound obtained as described in example 3, was obtained.

EXAMPLE 5

(2S,3R)-3-benzyloxycarbonylamino-2-hydroxy-butanoic acid

A solution of (2S,3R)-3-benzyloxycarbonylamino-4-phenyl-2-hydroxy-butanamide (23 g; 0.07 moles), prepared as described in example 3 or 4, in dioxane (185 ml) and hydrochloric acid 1N was heated under reflux for one hour.

After cooling, most dioxane was evaporated under reduced pressure. An oil was separated and extracted with ethyl acetate (2×200 ml).

The collected organic phases were washed with an aqueous saturated sodium chloride solution and dried on sodium sulphate.

After evaporation of the solvent under reduced pressure, a crude (25 g) was obtained which, after suspension in isopropyl ether and filtration, was crystallized from isopropyl acetate (120 ml).

(2S,3R)-3-benzyloxycarbonylamino-2-hydroxy-butanoic acid (15.35 g; 66.6% yield) with m.p. 156°–158° C. (litt. 154°–156° C.) was obtained.

$[\alpha]_D^{20} = +82.9°$ (c=1%, acetic acid)

$^1$H-NMR (200 MHz, CD$_3$OD—TMS): delta (ppm): $\nu_A = 2.94 - \nu_B = 2.85$ (AB portion of an ABX system, $J_{AB} = 13.4$ Hz, $J_{AX} = 7.7$ Hz, $J_{BX} = 8.0$ Hz, 2H); 4.08 (d, 1H, J=2.3 Hz); 4.28 (m, 1H); $\nu_A = 5.01 - \nu_B = 4.99$ (ABq, $J_{AB} = 12.5$ Hz, 2H); 7.15–7.37 (m, 10H).

EXAMPLE 6

(2R)-2-benzyloxycarbonylamino-3-(4-methylsulfonyl-phenyl)-propan-1-ol

Sodium hydroxide 1N (1.1 l) was added at +5° C. and under stirring to a solution of (2R)-2-amino-3-(4-methylsulfonyl-phenyl)-propan-1-ol hydrochloride (107.6 g; 0.4 moles) in ethyl acetate (2 l).

A solution of benzylchloroformate (63 ml) in ethyl ether (430 ml) and sodium hydroxide 1N (400 ml) were added to the suspension dropwise contemporaneously, always at +5° C. and under stirring, keeping pH between 7 and 8.

At the end of the addition the temperature was left arising up to the room value and the phases were separated.

The aqueous phase was extracted with ethyl acetate (1 l) and the collected organic phases were washed with 5% hydrochloric acid, with 5% sodium bicarbonate and with water.

After drying on sodium sulphate and evaporation of the solvent under reduced pressure, an amorphous solid, which was purified by treatment with isopropyl ether or by column chromatography on silica gel using, first, methylene chloride and, then, ethyl acetate as eluents, was obtained.

(2R)-2-benzyloxycarbonylamino-3-(4-methylsulfonyl-phenyl)-propan-1-ol (132 g; 91% yield) was obtained with m.p. 110°-112° C.

$[\alpha]_D^{20} = +62.8°$ (c=1%, DMF)

1H-NMR (200 MHz, CDCl$_3$—TMS): delta (ppm): 7.84–7.26 (m, 9H); 5.26 (d, 1H); 5.05 (s, 2H); 4.02–3.85 (m, 1H); 3.68–3.50 (m, 2H); 3.01 (s, 3H); 2.95 (d, 2H); 2.50 (bs, 1H).

EXAMPLE 7

(2R)-2-benzyloxycarbonylamino-3-(4-methylsulfonyl-phenyl)-propanal

Dimethylsulfoxide (59.6 ml; 0.84 moles) dissolved in methylene chloride (60 ml) and, in succession, (2R)-2-benzyloxycarbonylamino-3-(4-methylsulfonyl-phenyl)-propan-1-ol 130 g; 0.357 moles), prepared as described in example 6, dissolved in methylene chloride (530 ml) and dimethylsulfoxide (10 ml) and, lastly, triethylamine (111.5 ml; 0.70 moles) were added dropwise, at −75° C. and under stirring to a solution of oxalyl chloride (34 ml; 0.4 moles) in methylene chloride (450 ml).

The temperature was left arising up to the room value and water (600 ml) was added.

The phases were separated and the organic phase was washed twice with water (500 ml).

After drying on sodium sulphate and evaporation of the solvent under reduced pressure, a solid (130 g) was obtained.

A small amount of this solid (4.8 g) was crystallized from acetonitrile and t.butylmethylether giving (2R)-2-benzyloxycarbonylamino-3-(4-methylsulfonyl-phenyl)-propanal 3.2 g; 64% yield) with m.p. 152°-155° C.

$[\alpha]_D^{20} = -105.5°$ (c=1%, DMF)

1H-NMR (200 MHz, CDCl$_3$—TMS): delta (ppm): 9.67 (s, 1H); 7.87–7.30 (m, 9H); 5.37 (d, 1H); 5.12 (ABq, 2H); 4.53 (s, 2H); 3.03 (s, 3H); $\nu_A=3.32$–$\nu_B=3.19$ (AB portion of an ABX system, $J_{AB}=14.1$ Hz, $J_{AX}=6.2$ Hz, $J_{BX}=6.8$ Hz, 2H).

EXAMPLE 8

3-benzyloxycarbonylamino-2-hydroxy-4-(4-methylsulfonyl-phenyl)butanonitrile

Trimethylsilylcyanide (25 ml; 0.20 moles) was added dropwise to a suspension of (2R)-2-benzyloxycarbonylamino-3-(4-methylsulfonyl-phenyl)-propanal (69.4 g; 0.19 moles), prepared as described in example 7, in methylene chloride (1 l), under stirring and at room temperature.

The solution obtained at the end of the addition was evaporated to dryness under reduced pressure.

The oily residue was dissolved in tetrahydrofuran (500 ml) and hydrochloric acid 1N (60 ml) was added to the solution.

After 30 minutes at room temperature, ethyl acetate (500 ml) and an aqueous saturated sodium chloride solution (500 ml) were added. The organic phase was separated and, after washing with an aqueous saturated sodium chloride solution, it was dried on sodium sulfate and evaporated to dryness under reduced pressure giving a crude (76 g).

A portion of this crude (74.5 g) was crystallized from acetonitrile (520 ml) giving 3-benzyloxycarbonylamino-2-hydroxy-4-(4-methylsulfonyl-phenyl)-butanonitrile (53 g; 73% yield).

From HPLC analysis (Beckman Ultrasphere RP 18 column 4.5×250 mm 5 μm—eluent water:acetonitrile=7:3, flow 1 ml/min UV 220 nm) the obtained product resulted to be a mixture (2S,3R):(2R,3R)=88.5:11.5.

m.p. 158°-161° C.

$[\alpha]_D^{20} = +91.5°$ (c=1%, DMF)

1H-NMR (200 MHz, CD$_3$OD—TMS): delta (ppm): $\nu_A=3.19$–$\nu_B=3.08$ (AB portion of an ABX system, $J_{AB}=13.5$ Hz, $J_{AX}=6.2$ Hz, $J_{BX}=9.0$ Hz, 2H); 3.20 (s, 3H); 4.38–4.81 (m, 1H); $\nu_A=5.13$–$\nu_B=5.06$ (ABq, $J_{AB}=12.3$ Hz, 2H); 7.08 (d, 1H); 7.33–7.50 (m, 5H); 7.83 (AA′BB′ system, 4H).

EXAMPLE 9

(2S,3R)-3-benzyloxycarbonylamino-2-hydroxy-4-(4-methylsulfonylphenyl)-butanamide 37% hydrochloric acid (500 ml) was added dropwise to a solution of 3-benzyloxycarbonylamino-2-hydroxy-4-(4-methylsulfonyl-phenyl)butanonitrile [diastereoisomeric mixture (2S,3R):(2R,3R)=88.5:11.5] (35 g; 0.09 moles), prepared as described in example 8, in dioxane (500 ml) at +10° C. and under stirring.

A precipitate formed and the suspension was kept under stirring at room temperature for 20 hours having again a solution at the end. To this solution water (5 l) was added slowly keeping the temperature at +10°:+15° C.

A precipitate formed which was filtered, washed with water and dried on P$_2$O$_5$ at 50° C. under vacuum giving (2S,3R)-3-benzyloxycarbonylamino-2-hydroxy-4-(4-methylsulfonyl-phenyl)-butanamide (24.8 g; 68% yield) with m.p. 186°-191° C.

HPLC analysis (Beckman Ultrasphere RP 18 4.5×250 mm 5 μm—eluent water:methanol=6:4, flow 1 ml/min UV 220 nm) did not show the presence of any trace of (2R,3R) diastereoisomer.

$[\alpha]_D^{20} = +56.5°$ (c=1%, DMF)

1H-NMR (200 MHz, CDCl$_3$—TMS): delta (ppm): $\nu_A=3.08$–$\nu_B=2.86$ (AB portion of an ABX system, $J_{AB}=13.9$ Hz, $J_{AX}=6.5$ Hz, $J_{BX}=9.0$ Hz, 2H); 2.46 (s, 3H); 3.92–4.11 (m, 1H); 4.38–4.63 (m, 2H).

EXAMPLE 10

(2S,3R)-3-benzyloxycarbonylamino-2-hydroxy-4-(4-methylsulfonylphenyl)-butanoic acid A solution of (2S,3R)-3-benzyloxycarbonylamino-2-hydroxy-4-(4-methylsulfonyl-phenyl)-butanamide (95.8 g; 0.235 moles), prepared as described in example 9, in dioxane (670 ml) and hydrochloric acid 1N (960 ml) was heated under reflux for 5 hours and then evaporated to dryness under reduced pressure.

The residue was suspended in water (1 l), filtered, washed with water and dried on P$_2$O$_5$ at 50° C. under vacuum.

(2S,3R)-3-benzyloxycarbonylamino-2-hydroxy-4-(4-methylsulfonylphenyl)-butanoic acid (85.7 g; 90% yield) was obtained with m.p. 168°-172° C.

$[\alpha]_D^{20} = +87.2°$ (c=1%, DMF)

$^1$H-NMR (200 MHz, CD$_3$OD—TMS): delta (ppm): 7.83 (m, 4H); 7.50-7.33 (m, 5H); 7.08 (d, 1H); $\nu_A$=5.13-$\nu_B$=5.06 (ABq, $J_{AB}$=12.3 Hz, 2H); 3.20 (s, 3H); $\nu_A$=3.08 (AB portion of an ABX system, $J_{AX}$=6.2 Hz, $J_{BX}$=9.0 Hz, $J_{AB}$=13.5 Hz, 2H); 4.81-4.38 (m, 1H); 4.27 (d, 1H, J=2.4 Hz).

EXAMPLE 11

(2R)-2-benzyloxycarbonylamino-3-(4-methylthio-phenyl)-propan-1-ol

Sodium hydroxide 1N (115 ml) and benzylchloroformate (16.21 ml; 0.114 moles) dissolved in ethyl ether (93 ml) were added dropwise, contemporaneously at 0° C., to a solution of (2R)-2-amino-3-(4-methylthio)-propan-1-ol (18.3 g; 0.092 moles) in water (109 ml) and tetrahydrofuran (55 ml).

The pH was kept between 8 and 9.

At the end of the addition, the temperature was left arising up to the room value; this temperature was kept for two hours and then the two phases were separated.

The aqueous phase was extracted with ethyl acetate (2×250 ml) and the collected organic phases were washed with a 5% hydrochloric acid solution and then with a 5% sodium bicarbonate solution. After drying on sodium sulphate, the solvent was evaporated under reduced pressure giving a crude (38 g) which was purified by chromatography on silica gel (70-230 mesh) using methylene chloride with a gradient of ethyl acetate as eluent.

(2R)-2-benzyloxycarbonylamino-3-(4-methylthio-phenyl)-propan-1-ol (25.6 g; 84% yield) was obtained with m.p. 115°-117° C.

$[\alpha]_D^{20} = +64.7°$ (c=1%, DMF)

$^1$H-NMR (200 MHz, CDCl$_3$—TMS): delta (ppm): 7.42-7.09 (m, 9H); 5.07 (s, 2H); 5.04 (d, 1H); 3.98-3.83 (m, 1H); 3.70-3.51 (m, 2H); 2.82 (d, 2H); 2.47 (s, 3H); 2.14 (bs, 1H).

EXAMPLE 12

(2R)-2-benzyloxycarbonylamino-3-(4-methylthio-phenyl)-propanal

Starting from (2R)-2-benzyloxycarbonylamino-3-(4-methylthiophenyl)-propan-1-ol (24.24 g; 0.073 moles), prepared as described in example 11, and working in a way similar to that described in example 7, (2R)-2-benzyloxycarbonylamino-3-(4-methylthio-phenyl)propanal (24 g) was obtained.

$^1$H-NMR (200 MHz, CDCl$_3$—TMS): delta (ppm): 9.63 (s, 1H); 7.43-7.01 (m, 9H); 5.32 (d, 1H); 5.12 (s, 2H); 4.49 (dd, 1H); 3.10 (d, 2H); 2.46 (s, 3H).

EXAMPLE 13

3-benzyloxycarbonylamino-2-hydroxy-4-(4-methylthiophenyl)-butanonitrile.

Trimethylsilylcyanide (10.17 ml; 0.081 moles) was added dropwise to a solution of (2R)-2-benzyloxycarbonylamino-3-(4-methylthiophenyl)-propanal (24 g; 0.073 moles), prepared as described in example 12, in methylene chloride (275 ml) keeping the reaction mixture under stirring at 0° C.

The temperature was left arising up to the room value and the mixture was kept under stirring at this temperature for 2 hours. Methylene chloride was evaporated under reduced pressure and the residue was treated with tetrahydrofuran (200 ml) and hydrochloric acid. 1N (20 ml).

After stirring at room temperature for 20 minutes, ethyl acetate (200 ml) and sodium chloride up to saturation of the aqueous phase were added. The phases were separated and the aqueous phase was extracted again with ethyl acetate (200 ml).

The collected organic phases were dried on sodium sulphate, filtered and concentrated under vacuum.

A precipitate formed which was filtered and dried under vacuum at 50° C.

3-benzyloxycarbonylamino-2-hydroxy-4-(4-methylthio-phenyl)-butanonitrile (14.2 g; 54.6% yield) was obtained with m.p. 123°-125° C.

$[\alpha]_D^{20} = +105.2°$ (c=1%, DMF)

$^1$H-NMR (200 MHz, CDCl$_3$—TMS): delta (ppm): 7.42-7.08 (m, 9H); 5.28 (d, 1H, J=7.9 Hz); 5.08 (ABq, $J_{AB}$=12.5 Hz, 2H); 4.63-4.38 (m, 2H); 4.11-3.92 (m, 1H); $\nu_A$=3.08-$\nu_B$=2.86 (AB portion of an ABX system, $J_{AB}$=13.9 Hz, $J_{AX}$=6.5 Hz, $J_{BX}$=9.0 Hz, 2H); 2.46 (s, 3H).

EXAMPLE 14

(2S,3R)-3-benzyloxycarbonylamino-2-hydroxy-4-(4-methylthio-phenyl)-butanoic acid methyl ester Hydrochloric acid 11N in methanol (58.6 ml) was added to a solution of 3-benzyloxycarbonylamino-2-hydroxy-4-(4-methylthio-phenyl)-butanonitrile (11.73 g; 0.0329 moles), prepared as described in example 13, in methylene chloride (300 ml), under stirring and at the temperature of 0° C.

After two hours at 0° C., water was added (200 ml), keeping always the temperature at 0:+10° C.

The phases were separated and the aqueous phase was extracted twice again with methylene chloride (200 ml).

The collected organic phases, after drying on sodium sulphate and evaporation of the solvent under reduced pressure, gave a solid residue (13.7 g) which was crystallized several times from methanol/water obtaining (2S,3R)-3-benzyloxycarbonylamino-2-hydroxy-4-(4-methylthio-phenyl)-butanoic acid methyl ester (8.45 g; 66% yield).

$[\alpha]_D^{20} = +104.7°$ (c=1%, DMF)

$^1$H-NMR (200 MHz, CDCl$_3$—TMS): delta (ppm): 7.37-7.14 (m, 9H); 4.99 (ABq, $J_{AB}$=12.6 Hz, 2H); 4.21 (m, 1H); 4.14 (d, 1H, J=2.38 Hz); 3.63 (s, 3H); $\nu_A$=2.89-$\nu_B$=2.80 (AB portion of an ABX system, $J_{AB}$=13.6 Hz, $J_{AX}$=6.97 Hz, $J_{BX}$=8.42 Hz, 2H); 2.44 (s, 3H).

EXAMPLE 15

(2S,3R)-3-benzyloxycarbonylamino-2-hydroxy-4-(4-methylthio-phenyl)-butanoic acid Sodium hydroxide 1N (15.2 ml) was added slowly to a solution of (2S,3R)-3-benzyloxycarbonylamino-2-hydroxy-4-(4-methylthio-phenyl)-butanoic acid methyl ester (5.5 g; 0.0142 moles), prepared as described in example 14, in methanol (242 ml).

After 24 hours at room temperature the mixture was acidified with 10% hydrochloric acid up to pH 5.

The solution was concentrated by evaporating under reduced pressure, water (100 ml) and ethyl acetate (100 ml) were added, 10% hydrochloric acid was added up to pH 1 and the phases were separated.

The aqueous phase was extracted twice again with ethyl acetate (100 ml) and the collected organic phases, after drying on sodium sulphate and evaporation of the solvent under reduced pressure, gave a solid residue (5.5 g).

The residue was crystallized from dichloroethane (80 ml) and ethyl acetate (15 ml) giving (2S,3R)-3-benzyloxycarbonylamino-2-hydroxy-4-(4-methylthio-phenyl)-butanoic acid (3.5 g; 65.6% yield) with m.p. 174°–177° C.

$[\alpha]_D^{20} = +100.8°$ (c=1%, DMF)

$^1$H-NMR (200 MHz, CD$_3$OD—TMS): delta (ppm): 7.37–7.13 (m, 9H); 6.81 (d, 1H); $\nu_A=5.03-\nu_B=4.96$ (ABq, $J_{AB}=12.6$ Hz, 2H); 4.32–4.17 (m, 1H); 4.10 (d, 1H, J=2.4 Hz); $\nu_A=2.90-\nu_B=2.81$ (AB portion of an ABX system, $J_{AB}=13.5$ Hz, $J_{AX}=7.3$ Hz, $J_{BX}=8.3$ Hz, 2H).

EXAMPLE 16

(2R,3S)-3-benzyloxycarbonylamino-2-hydroxy-4-(4-methylsulfonylphenyl)-butanoic acid Dimethylsulfoxide (63 ml; 0.9 moles) in methylene chloride (100 ml) and, in succession, (2S)-2-benzyloxycarbonylamino-3-(4-methylsulfonyl-phenyl)-propan-1-ol (100 g; 0.275 moles) dissolved in a mixture of methylene chloride (500 ml) and dimethylsulfoxide (10 ml) were added dropwise, at −20° C., to a mixture of oxalyl chloride (38 ml; 0.44 moles) and methylene chloride (400 ml) and, after one hour, trimethylsilylcyanide (51 ml; 0.38 moles) were added dropwise keeping always the temperature at −20° C.

The temperature was left arising very slowly up to the room value and then the reaction mixture was poured into water (500 ml). The phases were separated; the organic phase was washed with water (500 ml) and evaporated to dryness.

The residue was dissolved in dioxane (1 l) and concentrated hydrochloric acid (1 l) was added to the solution at +10° C.

After 18 hours under stirring at room temperature, a sodium hydroxide solution was added dropwise up to pH 3 and the product was extracted with ethyl acetate (3×300 ml).

After evaporation of the organic solvent, the residue was dissolved in a mixture of dioxane (790 ml) and hydrochloric acid 1N (0.1130 ml).

The solution was heated under reflux for 6 hours, colled to room temperature and then extracted with ethyl acetate (3×300 ml). The collected organic phases were treated with a 5% sodium bicarbonate solution (500 ml); the aqueous phase was separated, acidified with hydrochloric acid and extracted with ethyl acetate (2×300 ml).

The collected organic phases were dried on sodium sulphate and evaporated to dryness.

The obtained solid residue (93 g) was crystallized from acetonitrile (200 ml) giving (2R,3S)-3-benzyloxycarbonylamino-2-hydroxy-4-(4-methylsulfonyl-phenyl)-butanoic acid (46 g; overall yield 41%) with m.p. 168°–170° C.

$[\alpha]_D^{20} = -84.0°$ (c=1%, DMF)

By working in a similar way the following compounds were prepared:

(2S,3R)-3-benzyloxycarbonylamino-2-hydroxy-4-(4-methylsulfonylphenyl)-butanoic acid overall yield 39.6%
m.p. 168°–170° C.
$[\alpha]_D^{20} = +84.0°$ (c=1%, DMF)

(2R,3S)-3-benzyloxycarbonylamino-2-hydroxy-4-phenyl-butanoic acid overall yield 35.1%
m.p. 154°–156° C.
$[\alpha]_D^{20} = -82.5°$ (c=1%, acetic acid).

What we claim is:

1. A diastereoselective process for the preparation of compounds of formula

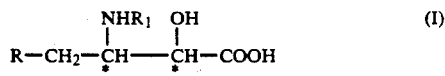

wherein

R represents a phenyl optionally substituted by from 1 to 3 substituents selected among hydroxy, halogen, C$_1$–C$_6$ alkoxy, C$_1$–C$_6$ alkyl, phenyl, amino, mono or dialkylamino groups having from 1 to 6 carbon atoms in the alkyl moiety, nitro, mercapto, alkylthio, alkylsulfinyl or alkylsulfonyl groups having from 1 to 6 carbon atoms in the alkyl moiety;

R$_1$ represents a protecting group; and, the asterisks show the asymmetric carbon atoms; comprising the transformation of an aldehyde of formula

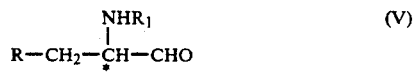

wherein R and R$_1$ have the meanings reported for formula I; into a cyanohydrin of formula

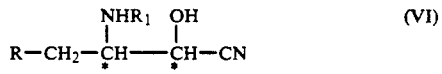

wherein R and R$_1$ have the meanings reported for formula I; by reaction with a suitable silylcyanide in an aprotic solvent at a temperature between −80° C. and room temperature and by subsequent hydrolysis of the obtained compound of formula VI.

2. A process according to claim 1 wherein the aldehyde of formula V is prepared from an aminoalcohol of formula

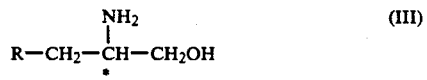

wherein

R has the meanings reported in claim 1;

by protection of the amino function and oxidation.

3. A process according to claim 1 wherein the hydrolysis of the compound of formula VI is carried out by treatment with concentrated inorganic acids at a temperature between 0° C. and room temperature in order to obtain the intermediate of formula

wherein

R and $R_1$ have the meanings reported in claim 1 and $R_4$ represents a $NH_2$ or $C_1$-$C_3$ alkoxy group;
which, by treatment with a diluted inorganic acid or base at a temperature between 60° C. and the reflux temperature of the reaction mixture, gives a compound of formula I.

4. A process according to claim 1 wherein the silylcyanide is selected among trimethylsilylcyanide, triphenylsilylcyanide, ethyldimethylsilylcyanide, t.butyldimethylsilylcyanide and tripropylsilylcyanide.

5. A process according to claim 1 wherein the silylcyanide is trimethylsilylcyanide.

6. A process according to claim 1 wherein the temperature, in the reaction between compound V and the silylcyanide, is between −80° C. and −20° C.

* * * * *